United States Patent [19]

Böshagen et al.

[11] Patent Number: 5,079,258
[45] Date of Patent: Jan. 7, 1992

[54] TETRAHYDRO-1-BENZ-(C,D)-INDOLEPROPIONIC ACID SULPHONAMIDES AS THROMBOCYTE AGGREGATION INHIBITORS

[75] Inventors: Horst Böshagen, Haan; Ulrich Rosentreter; Elisabeth Perzborn, both of Wuppertal; Volker-Bernd Fiedler, Leverkusen, all of Fed. Rep. of Germany

[73] Assignee: Bayer Aktiengesellschaft, Leverkusen, Fed. Rep. of Germany

[21] Appl. No.: 384,531

[22] Filed: Jul. 24, 1989

[30] Foreign Application Priority Data

Aug. 3, 1988 [DE] Fed. Rep. of Germany ....... 3826371

[51] Int. Cl.$^5$ .................. A61K 31/405; C07D 209/90
[52] U.S. Cl. ..................................... 514/411; 548/436
[58] Field of Search ......................... 548/436; 514/411

[56] References Cited

U.S. PATENT DOCUMENTS 4,853,406  8/1989  Rosentreter et al. ............... 548/436

FOREIGN PATENT DOCUMENTS 3613623 10/1987  Fed. Rep. of Germany ...... 548/436
3631824  3/1988  Fed. Rep. of Germany ...... 548/436

Primary Examiner—Robert Gerstl
Attorney, Agent, or Firm—Sprung, Horn Kramer & Woods

[57] ABSTRACT

Tetrahydro-1-benz-[c,d],indolepropionic acid sulphonamides of the formula

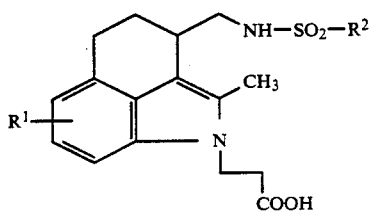

can be prepared by reaction of tetrahydro-1-benz-[c,d]-indolesulphonamides with acrylonitrile and subsequent hydrolysis. The new compounds can be employed inhibiting thrombocyte aggregation.

24 Claims, No Drawings

TETRAHYDRO-1-BENZ-(C,D)-INDOLEPROPIONIC ACID SULPHONAMIDES AS THROMBOCYTE AGGREGATION INHIBITORS

The invention relates to new tetrahydro-1-benz-[c,d]-indolepropionic acid sulphonamides, processes for their preparation and their use in medicaments.

It has been disclosed that cycloalkano-(1,2-b)-indole- and N-dihydroindolylethyl sulphonamides have a thrombocyte aggregation-inhibiting effect (DE-A 3,631,824 and 3,613,623).

New tetrahydro-1-benz-[c,d]-indolepropionic acid sulphonamides of the general formula (I)

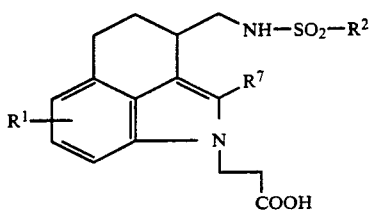

in which

R$^1$ - represents hydrogen, halogen, trifluoromethyl, carboxyl, alkoxycarbonyl or -represents a group —S(O)$_n$R$^3$, —NR$^4$R$^5$ or OR$^6$, in which R$^3$ -denotes alkyl or aryl, R$^4$ and R$^5$ are identical or different and denote hydrogen, alkyl, aryl or aralkyl, R$^6$ - denotes hydrogen, alkyl aryl, aralkyl or trifluoromethyl, and n - denotes a number 0, 1 or 2, or R$^1$ - represents alkyl, alkenyl or cycloalkyl, which is optionally substituted by carboxyl, alkoxycarbonyl, halogen, hydroxyl, alkoxy, alkylthio or cyano, and R$^2$ - represents aryl having 6 to 10 carbon atoms which is monosubstituted to trisubstituted by identical or different halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy or benzylthio, or by a group of the formula —NR$^4$R$^5$, in which R$^4$ and R$^5$ have the abovementioned meanings, R$^7$ represents hydrogen, alkyl or cycloalkyl and their salts, have now been found.

The compounds according to the invention can exist in various stereochemical forms. The invention relates both to the individual isomers and to their mixtures

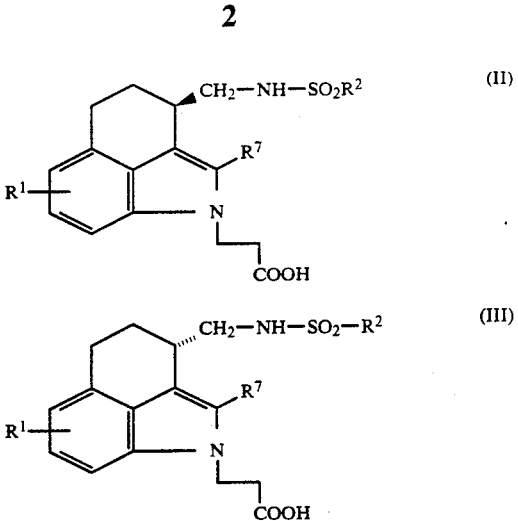

The compounds according to the invention can also exist in the form of their salts. In general, salts with organic or inorganic bases may be mentioned here.

In the context of the present invention, physiologically acceptable salts are preferred. Physiologically acceptable salts may be metal or ammonium salts of the substances according to the invention which have a free carboxyl group. For example, salts of sodium, potassium, magnesium or calcium and ammonium salts which are derived from ammonia or organic amines such as, for example, ethylamine, di- or triethylamine, di- or triethanolamine, dicyclohexylamine, dimethylaminoethanol, arginine or ethylenediamine are particularly preferred.

The substances according to the invention surprisingly show a thrombocyte aggregation-inhibiting effect and can be used for therapeutic treatment of humans and animals.

Alkyl in general represents a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general represents a straight-chain or branched hydrocarbon radical having 2 to 12 carbon atoms and having one or more, preferably one or two, double bonds. The lower alkenyl radical having 2 to about 6 carbon atoms and one double bond is preferred. An alkenyl radical having 2 to 4 carbon atoms and one double bond is particularly preferred. Examples which may be mentioned are vinyl, allyl, propenyl, isopropenyl, butenyl, isobutenyl, pentenyl, isopentenyl, hexenyl, isohexenyl, heptenyl, isoheptenyl, octenyl and isooctenyl.

Cycloalkyl in general represents a cyclic hydrocarbon radical having 3 to 8 carbon atoms. The cyclopropyl, cyclopentane and the cyclohexane ring are preferred. Examples which may be mentioned are cyclopentyl, cyclohexyl, cycloheptyl and cyclooctyl.

Alkoxy in general represents a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general represents a straight-chain or branched hydrocarbon radical having 1 to 12 carbon atoms which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

Aryl in general represents an aromatic radical having 6 to about 12 carbon atoms. Preferred aryl radicals are phenyl, naphthyl and diphenyl.

Aralkyl in general represents an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Alkoxycarbonyl may be represented, for example, by the formula

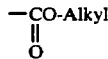

Alkyl in this connection represents a straight-chain or branched hydrocarbon radical having 1 to 8 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Carboxyalkyl in general represents a straight-chain or branched hydrocarbon radical having 1 to 12 carbon atoms which is substituted by a carboxyl group. Carboxy lower alkyl having 1 to about 6 carbon atoms is preferred. Examples which may be mentioned are: carboxymethyl, 1-carboxyethyl, 1-carboxypropyl, 1-carboxybutyl, 1-carboxypentyl, 1-carboxyhexyl, 2-carboxyethyl, 2-carboxypropyl, 2-carboxybutyl, 3-carboxypropyl, 3-carboxybutyl, 4-carboxybutyl, 2-carboxy-1-propyl or 1-carboxy-1-propyl.

Alkoxycarbonylalkyl in general represents a straight-chain or branched hydrocarbon radical having 1 to 12 carbon atoms which is substituted by an alkoxycarbonyl group, alkoxycarbonyl having the abovementioned meaning. Lower alkoxycarbonyl lower alkyl in each case having 1 to about 6 carbon atoms in each alkyl moiety is preferred.

Examples which may be mentioned are: methoxycarbonylmethyl, ethoxycarbonylmethyl, propoxycarbonylmethyl, butoxycarbonylmethyl, isopropoxycarbonylmethyl, isobutoxycarbonylmethyl, 1-methoxycarbonylethyl, 1-ethoxycarbonylethyl, 1-propoxycarbonylethyl, 1-butoxycarbonylethyl, 1-isopropoxycarbonylethyl, 1-isobutoxycarbonylethyl, 2-methoxycarbonylethyl, 2-ethoxycarbonylethyl, 2-propoxycarbonylethyl, 2-butoxycarbonylethyl, 2-isopropoxycarbonylethyl, 2-isobutoxycarbonylethyl, 2-methoxycarbonyl-2-propyl, 2-ethoxycarbonyl-2-propyl, 2-propoxycarbonyl-2-propyl, 2-butoxycarbonyl-2-propyl, 2-isopropoxycarbonyl-2-propyl, 2-isobutoxycarbonyl-2-propyl, 2-methoxycarbonyl-2-propyl, 1-ethoxycarbonyl-2-propyl, 2-propoxycarbonyl-2-propyl, 1-butoxycarbonyl-2-propyl, 1-isopropoxycarbonyl-2-propyl, 1-isobutoxycarbonyl-2-propyl, 3-methoxycarbonylpropyl, 3-ethoxycarbonylpropyl, 3-isopropoxycarbonylpropyl or 3-isobutoxycarbonylpropyl.

Halogen in general represents fluorine, chlorine, bromine or iodine, preferably fluorine, chlorine or bromine. Halogen particularly preferably represents fluorine or chlorine.

Compounds of the general formula (I) are preferred in which $R^1$ - represents hydrogen, fluorine, chlorine, bromine, trifluoromethyl, carboxyl or lower alkoxycarbonyl, or

- represents a group $-S(O)_nR^3$, $-NR^4R^5$ or $OR^6$, in which $R^3$ - denotes lower alkyl or phenyl, $R^4$ and $R^5$ are identical or different and

- denote hydrogen, lower alkyl, phenyl or benzyl, $R^6$- denotes hydrogen, lower alkyl, phenyl, benzyl or trifluoromethyl, and n - denotes a number 0 or 2, or $R^1$ - represents lower alkyl, lower alkenyl, cyclopropyl, cyclopentyl or cyclohexyl, which is optionally substituted by carboxyl, lower alkoxy, fluorine, chlorine, bromine, hydroxyl, lower alkoxycarbonyl, lower alkylthio or cyano, and $R^2$ - represents phenyl or naphthyl, which is monosubstituted to trisubstituted by identical or different fluorine, chlorine, bromine, cyano, trifluoromethyl, trifluoromethoxy, trifluoromethylthio, lower alkyl, carboxymethyl, carboxyethyl, methoxycarbonylmethyl, methoxycarbonylmethyl, ethoxycarbonylmethyl, methoxycarbonylethyl, lower alkoxy, lower alkylthio, hydroxyl, carboxyl, lower alkoxycarbonyl, phenyl, phenoxy, benzyloxy or benzylthio, or by a group of the formula $-NR^4R^5$, in which $R^4$ and $R^5$ have the abovementioned meanings, $R^7$ - represents hydrogen, lower alkyl, cyclopropyl, cyclopentyl or cyclohexyl and their salts.

Particularly preferred compounds of the general formula (I) are those in which $R^1$ - represents hydrogen, fluorine, chlorine, bromine, trifluoromethyl, methylthio, ethylthio, methylsulphonyl, ethylsulphonyl, phenylthio, phenylsulphonyl, amino, dimethylamino or diethylamino, or

- represents a group $-OR^6$, in which $R^6$ - denotes hydrogen, methyl, ethyl, propyl, phenyl or benzyl or

- represents methyl, ethyl, propyl or isopropyl, $R^2$ - represents phenyl or naphthyl, which is monosubstituted or disubstituted by identical or different fluorine, chlorine, bromine, cyano, trifluoromethyl, trifluoromethoxy, methyl, ethyl, propyl, methoxy, ethoxy, propoxy, methylthio, hydroxyl, methoxycarbonyl, ethoxycarbonyl, phenyl, dimethylamino or diethylamino, $R^7$ - represents hydrogen or methyl, and their salts.

Very particularly preferred compounds of the general formula (I) are those in which R¹ - denotes hydrogen or fluorine,
R² - represents phenyl or naphthyl, which is substituted by fluorine, chlorine, bromine, methyl, methoxy or phenyl,
R⁷ - represents methyl, and their salts.

The following may be mentioned as examples:
2-Methyl-3-(benzenesulphonyl)-aminomethyl-1,3,4,5-tetrahydro-1-benz-[c,d]-indolepropionic acid
2-Methyl-3-(4-fluorobenzenesulphonyl)-aminomethyl-1,3,4,5-tetrahydro-1-benz-[c,d]-indolepropionic acid
2-Methyl-3-(4-bromobenzenesulphonyl)-aminomethyl-1,3,4,5-tetrahydro-1-benz-[c,d]-indolepropionic acid
2-Methyl-3-(4-chlorobenzenesulphonyl)-aminomethyl-1,3,4,5-tetrahydro-1-benz-[c,d]-indolepropionic acid
2-Methyl-3-(4-toluenesulphonyl)-aminomethyl-1,3,4,5-tetrahydro-1-benz-[c,d]-indolepropionic acid
2-Methyl-3-(4-methoxybenzenesulphonyl)-aminomethyl-1,3,4,5-tetrahydro-1-benz-[c,d]-indolepropionic acid
2- Methyl-3-(1-naphthylsulphonyl)-aminomethyl-1,3,4,5-tetrahydro-1-benz-[c,d]-indolepropionic acid (Na salt).

A process for the preparation of tetrahydro-1-benz-[c,d]-indolepropionic acid sulphonamides of the general formula (I)

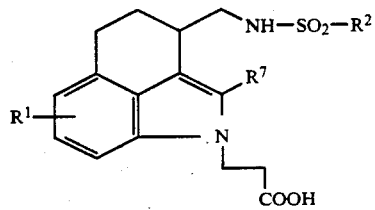

in which

R¹, R² and R⁷ have the abovementioned meanings, has been found, which is characterized in that tetrahydro-1-benz-[c,d]-indolesulphonamide compounds of the general formula (IV)

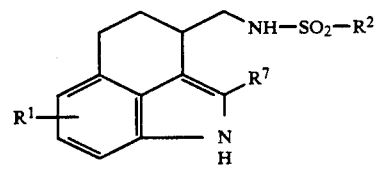

in which

R¹, R² and R⁷ have the abovementioned meanings, are reacted with acrylonitrile of the formula (V)

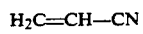

in the presence of an inert solvent and if appropriate in the presence of a base to give the compounds of the general formula (VI)

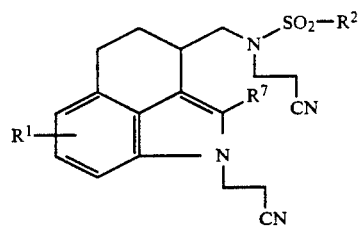

in which

R¹, R² and R⁷ have the abovementioned meanings, and the N,N'-biscyanoethyl compounds (VI) are then hydrolyzed.

The process according to the invention can be illustrated by the following equation:

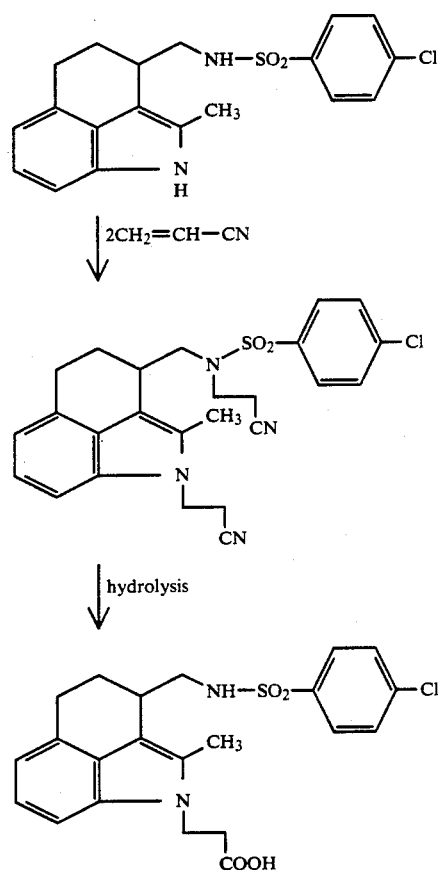

Solvents for the process according to the invention may be inert organic solvents which do not change under the reaction conditions. These preferably include alcohols such as methanol, ethanol, propanol or isopropanol, ethers such as diethyl ether, tetrahydrofuran, dioxane, glycol monomethyl or glycol dimethyl ether, hydrocarbons such as benzene, toluene, xylene, cyclohexane, hexane or mineral oil fractions, dimethyl sulphoxide, dimethylformamide, hexamethylphosphoramide, ethyl acetate or pyridine. It is also possible to use mixtures of the solvents mentioned.

Bases for the process according to the invention may be customary basic compounds. These preferably include alkali metal hydroxides and alkaline earth metal hydroxides such as lithium hydroxide, sodium hydroxide, potassium hydroxide or barium hydroxide, alkali metal hydrides such as sodium hydride, alkali metal carbonates or alkaline earth metal carbonates such as sodium carbonate, potassium carbonate, or alkali metal alkoxides such as, for example, sodium methoxide or ethoxide, potassium methoxide or ethoxide or potassium tert.-butoxide, or organic amines such as benzyl-trimethyl-ammonium hydroxide, tetrabutylammonium hydroxide, pyridine, triethylamine or N-methylpiperidine.

The process according to the invention is in general carried out in a temperature range from 0° C. to 150° C., preferably from 20° C. to 100° C.

The process according to the invention is in general carried out at atmospheric pressure. However, it is also possible to carry out the process at subatmospheric pressure or at excess pressure (for example in a range from 0.5 to 5 bar).

In general, 2 to 20 moles, preferably 2 to 10 moles, of acrylonitrile are employed relative to 1 mole of [arylsulphonaminoalkyl]-1,3,4,5-tetrahydro-benz-[c,d]-indole.

Hydrolysis of the N,N'-bis-cyanoethyl compounds is carried out in a manner known per se in the presence of bases, such as alkali metal hydroxides or alkoxides or alkaline earth metal hydroxides or alkoxides, in inert solvents such as water or alcohols. Preferably, sodium hydroxide, potassium hydroxide or barium hydroxide, sodium methoxide, potassium methoxide, sodium ethoxide or potassium ethoxide are employed as bases, preferably in water or methanol, ethanol, propanol or isopropanol or in mixtures of these solvents.

In general, 1 to 100 moles, preferably 2 to 50 moles, of base are employed relative to 1 mole of N,N'-biscyanoethyl compound.

Hydrolysis is carried out in a temperature range from 0° C. to 100° C., preferably from 20° C. to 80° C.

The compounds of the general formula (IV) are new. A process for preparation has likewise been found, which is characterized in that indoles of the general formula (VII)

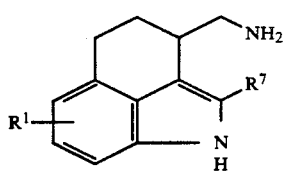

(VII)

in which
R$^1$ and R$^7$ have the abovementioned meanings,
are reacted with sulphonyl halides of the general formula (VIII)

$$X-SO_2-R^2 \quad (VIII)$$

in which
R$^2$ - has the abovementioned meaning
and
X - represents halogen,
in inert solvents, if appropriate in the presence of a base.

The reaction may be illustrated by the following equation:

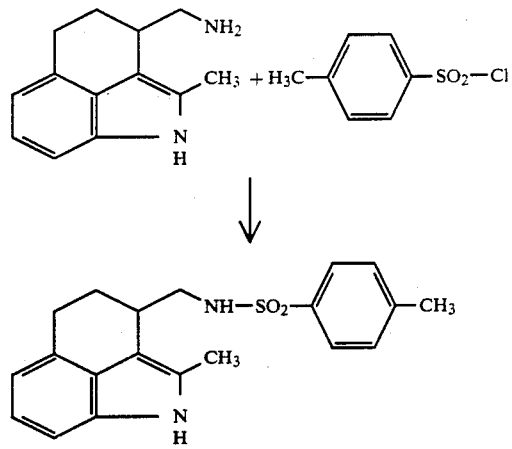

Solvents for the process according to the invention may be inert organic solvents which do not change under the reaction conditions. These preferably include alcohols, such as, for example, methanol, ethanol, n-propanol, isopropanol, glycol, ethers, such as, for example, diethyl ether, dioxane, tetrahydrofuran, glycol monomethyl or glycol dimethyl ether, halogenated hydrocarbons such as di-, tri- or tetrachloromethane, dichloroethylene, trichloroethylene, ethyl acetate, toluene, acetonitrile, glacial acetic acid, hexamethylphosphoramide, pyridine and acetone. Of course, it is possible to employ mixtures of these solvents.

Bases for the process according to the invention may be customary basic compounds. These preferably include alkali metal hydroxides and alkaline earth metal hydroxides such as lithium hydroxide, sodium hydroxide, potassium hydroxide or barium hydroxide, alkali metal hydrides such as sodium hydride, alkali metal carbonates or alkaline earth metal carbonates such as sodium carbonate, potassium carbonate, or alkali metal alkoxides such as, for example, sodium methoxide or ethoxide, potassium methoxide or ethoxide or potassium tert.-butoxide, or organic amines such as benzyltrimethylammonium hydroxide, tetrabutylammonium hydroxide, pyridine, triethylamine or N-methylpyridine.

The process according to the invention is in general carried out in a temperature range from 0° C. to 150° C., preferably at 25°–40° C.

The process according to the invention is in general carried out at atmospheric pressure. However, it is also possible to carry out the process at subatmospheric pressure or at excess pressure (for example in a range from 0.5 to 5 bar).

In general, 1 to 5 moles, preferably 1 to 2 moles, particularly preferably 1 mole, of sulphonyl halide is employed relative to 1 mole the 3-(1-aminoalkyl)-1,3,4,5-tetrahydrobenz-[c,d]-indole.

Sulphonyl halides which can be used according to the invention are, for example:
Benzenesulphonyl chloride
4-Fluorobenzenesulphonyl chloride
4-Bromobenzenesulphonyl chloride
4-Chlorobenzenesulphonyl chloride
4-Toluenesulphonyl chloride
4-Methoxybenzenesulphonyl chloride
1-Naphthylsulphonyl chloride The compounds of the general formula (VII) are known or can be prepared by a known method (NL-A 6,409,079).

The sulphonyl halides of the general formula (VIII) and acrylonitrile of the formula (V) are known [Houben-Weyls "Methoden der organischen Chemie" ("Methods of Organic Chemistry"), Volume IX, p. 407 ff. and p. 547 ff. (1959)].

The new tetrahydro-1-benz-[c,d]-indolepropionic acid sulphonamides or their salts can be employed as active compounds in medicaments. The active compounds have a thrombocyte aggregation-inhibiting and thromboxane $A_2$-antagonistic effect. They may preferably be employed for the treatment of thromboses, thromboembolisms, ischaemias, as anti-asthmatics and as anti-allergics. The new active compounds can be converted in a manner known per se using inert non-toxic, pharmaceutically suitable excipients or solvents into the customary formulations, such as tablets, capsules, coated tablets, pills, granules, aerosols, syrups, emulsions, suspensions and solutions. In this case, the therapeutically active compound should in each case be present in a concentration of about 0.5 to 90% by weight, preferably of 5 to 70% by weight, relative to the preparation, which is sufficient in order to achieve the dosage range indicated.

The formulations are prepared, for example, by extending the active compounds with solvents and/or excipients, optionally using emulsifiers and/or dispersants, where, for example, in the case of the use of water as a diluent, if appropriate organic solvents can be used as auxiliary solvents.

Auxiliaries which may be mentioned are, for example: water, non-toxic organic solvents such as paraffins (for example mineral oil fractions), vegetable oils (for example groundnut/sesame oil), alcohols (for example ethyl alcohol, glycerol), glycols (for example propylene glycol, propylethylene glycol), solid excipients, such as, for example, ground natural minerals (for example kaolins, aluminas, talc, chalk), ground synthetic minerals (for example highly-disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium lauryl sulphate).

Administration may be carried out in a customary manner, preferably orally or parenterally, in particular perlingually or intravenously. In the case of oral administration, tablets may, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc may additionally be used for tabletting. In the case of aqueous suspensions and/or elixirs which are intended for oral administration, various flavor-improvers or colorants may be added to the active compounds in addition to the abovementioned auxiliaries.

In the case of parenteral administration, solutions of the active compounds may be employed using suitable liquid excipients.

In general, it has proved advantageous on intravenous administration to administer amounts of about 0.001 to 1 mg/kg, preferably about 0.01 to 0.05 mg/kg, of body weight to obtain effective results. On oral administration, the dosage is in general about 0.01 to 20 mg/kg, preferably 0.1 to 10 mg/kg, of body weight.

However, it may optionally be advantageous to deviate from the amounts mentioned, depending on the body weight or the type of application route, on the individual behavior towards the medicament, the manner of its formulation and the point in time or interval at which administration takes place. Thus, in some cases it may be sufficient to manage with less than the minimum amount previously mentioned, whereas in other cases the upper limit mentioned must be exceeded. In the case of administration of larger amounts, it may be advisable to divide these into a number of individual doses over the day.

The tetrahydro-1-benz-[c,d]-indolepropionic acid sulphonamides according to the invention may be used both in human medicine and in veterinary medicine.

PREPARATION AND USE EXAMPLES

EXAMPLE 1

2-Methyl-indole-3-succinic acid

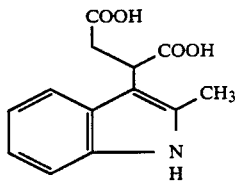

A mixture of 13.1 g (0.1 mol) of 2-methylindole and 11.6 g (0.1 mol) of maleic acid are heated on a water bath until it solidifies. The mixture is then allowed to stand for 30 minutes. A solution of 11.3 g (0.2 mol) of potassium hydroxide in 200 ml of water is subsequently added and the mixture is heated with stirring for 30 minutes. After cooling, the solution is extracted using ether and treated with active carbon, filtered, cooled and acidified using HCl. The residue is then filtered off and washed with water.

M.p.: 210°–211° C. (decomposition)

TLC: $CHCl_3/CH_3OH = 3:1$, silica gel on aluminum foil/Merck 5562

$R_f = 0.32$

Yield: 17.2 g (69.6% of theory)

EXAMPLE 2

5-Fluoro-2-methylindole-3-succinic acid

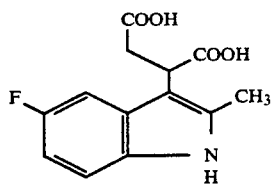

The title compound was prepared analogously to the directions of Example 1.

M.p.: 220° C.

TLC: $CHCl_3/CH_3OH = 3:1$, silica gel on aluminum foil/Merck 5562

$R_f = 0.21$

Yield: 57.1%

EXAMPLE 3

1-Acetyl-2-methyl-3-indolesuccinic anhydride

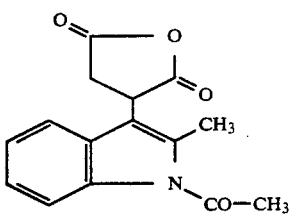

A mixture of 24.7 g (0.1 mol) of 2-methyl-3-indolesuccinic acid, 200 ml of isopropenyl acetate and 2 g (0.011 mol) of p-toluenesulphonic acid monohydrate is heated under reflux for 30 minutes. The acetone is slowly removed by distillation. The solution is concentrated in vacuo and the residue is crystallized from 60 ml of acetic acid and 15 ml of acetic anhydride.

M.p.: 192°–193° C.
TLC: $CHCl_3/CH_3OH=3:1$, silica gel on aluminum foil/Merck 5562
$R_f=0.71$
Yield: 12.1 g (44.6% of theory)

EXAMPLE 4

1-Acetyl-5-fluoro-2-methyl-3-indolesuccinic anhydride

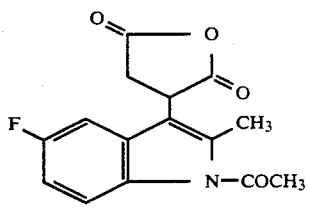

The title compound was prepared analogously to the directions of Example 3.

M.p.: 178° C.
TLC: $CHCl_3/CH_3OH=3:1$, silica gel on aluminum foil/Merck 5562
$R_f=0.65$
Yield: 47.6%

EXAMPLE 5

1-Acetyl-2-methyl-1,3,4,5-tetrahydro-5-oxo-benz-[c,d]-indole-3-carboxylic acid

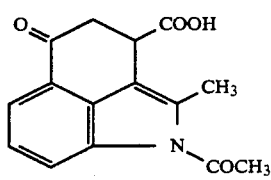

2.71 g (0.01 mol) of the compound from Example 3 are dissolved in 60 ml of warm ethylene dichloride. The solution is cooled with stirring until a fine suspension appears. 6.67 g (0.05 mol) of aluminum chloride are added at room temperature to a suspension of 60 ml of anhydride in 60 ml of ethylene dichloride. The solution is heated at 40° C. for 4 h, cooled and 50 ml of 2 N HCl are added. The residue is filtered off, washed with water and dissolved in warm acetone. The solution is treated with active carbon and crystallized by cooling.

M.p.: 215°–217° C.
TLC: $CHCl_3/CH_3OH=3:1$, silica gel on aluminum foil/Merck 5562
$R_f=0.50$
Yield: 0.75 g (27.7%)

EXAMPLE 6

1-Acetyl-6-fluoro-2-methyl-1,3,4,5-tetrahydro-5-oxo-benz-[c,d]-indole-3-carboxylic acid

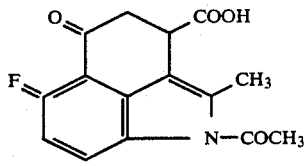

The title compound was prepared from 0.27 g (0.01 mol) of the compound from Example 4 analogously to the directions of Example 5.

M.p.: 248° C. (decomposition)
TLC: $CHCl_3/CH_3OH=3:1$, silica gel on aluminum foil/Merck 5562
$R_f=0.36$
Yield: 82.4%

EXAMPLE 7

2-Methyl-1,3,4,5-tetrahydro-5-oxobenz-[c,d]-indole-3carboxylic acid

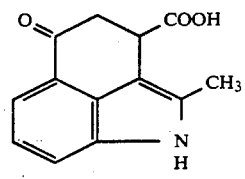

A solution of 1 g (0.0037 mol) of the compound from Example 5 and 50 ml of 0.2 N NaOH is allowed to stand at room temperature for 3 h and then acidified using dilute hydrochloric acid. The product which precipitates is filtered off, washed with water and recrystallized from dilute acetic acid.

M.p.: 235°–239° C.
TLC: $CHCl_3/CH_3OH=3:1$, silica gel on aluminum foil/Merck 5562
$R_f$ 0.50
Yield: 0.60 g (71.4% of theory)

EXAMPLE 8

2-Methyl-1,3,4,5,-tetrahydrobenz-[c,d]-indole-3-carboxylic acid

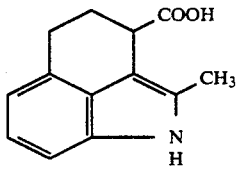

22.9 g (0.1 mol) of the compound from Example 7 and 0.5 mol of hydrazine hydrate (85% strength solution) are added at room temperature to a cooled solution of NaOH (0.5 mol) in 250 ml of diethylene glycol. The mixture is heated under reflux for 20 minutes, cooled, diluted using 500 ml of water and extracted using ether.

The aqueous solution is cooled in an ice bath, acidified using conc. HCl and extracted using ether. The ethereal solution is washed with water, dried over magnesium sulphate and concentrated in vacuo.

The residue is dissolved in chloroform and treated with active carbon; this is subsequently filtered off and the solution is concentrated and cooled. The product precipitates in yellow platelets.

M.p.: 103° C.
TLC: Toluene/C₂H₅OH=3:1, silica gel on aluminum foil/Merck 5562
$R_f$: 0.53
Yield: 14.2 g (66.0% of theory)

EXAMPLE 9

6-Fluoro-2-methyl-1,3,4,5-tetrahydrobenz-[c,d]-indole-3-carboxylic acid

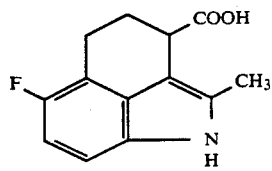

The title compound is prepared analogously to the directions of Example 8 using 22.9 g (0.1 mol) of the compound from Example 6.

M.p.: 190° C.
TLC : Toluene/ethanol=3:1, silica gel on aluminum foil / Merck 5562
$R_f$: 0.55
Yield: 53.8%

EXAMPLE 10

2-Methyl-1,3,4,5-tetrahydrobenz-[c,d]-indole-3-carboxamide

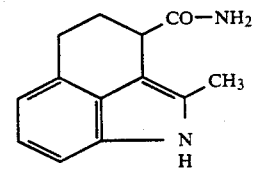

4.30 g (0.02 mol) of the compound from Example 8 are dissolved in 50 ml of absolute tetrahydrofuran and 3.89 g (0.024 mol) of N,N'-carbonyldiimidazole are added. The mixture is stirred overnight and concentrated, and the residue is taken up in methylene chloride. The solution is then washed twice with water, dried over magnesium sulphate and concentrated, and the residue is dissolved in 50 ml of absolute tetrahydrofuran. 20 ml of 5 N methanolic ammonia solution is subsequently added. The mixture is stirred at room temperature for 2 h and concentrated, and the product is crystallized from ethyl acetate.

M.p.: 218° C.
TLC : CH₂Cl₂/ethyl acetate 1:1, silica gel on aluminum foil / Merck 5562
$R_f$=0.21
Yield: 3.50 g (81.8 % of theory)

EXAMPLE 11

6-Fluoro-2-methyl-1,3,4,5-tetrahydrobenz-[c,d]-indole-3-carboxamide

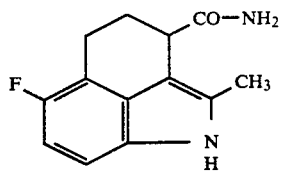

The title compound is prepared from 4.3Q g (0.02 mol of the compound from Example 9 analogously to the directions of Example 10.

M.p.: 230° C.
TLC : CH₂Cl₂/ethyl acetate 1:1, silica gel on aluminum foil / Merck 5562
$R_f$: 0.20
Yield: 68.8%

EXAMPLE 12

3-Aminomethyl-2-methyl-1,3,4,5-tetrahydrobenz-[c,d]-indole

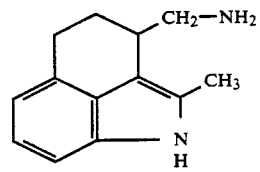

3.21 g (0.015 mol) of the compound from Example 10 are suspended in 70 ml of absolute tetrahydrofuran. 30 ml of a 1-molar (0.03 mol) lithium aluminum hydride solution in tetrahydrofuran are then added dropwise at room temperature. The mixture is then stirred at reflux temperature for 2 h, 20 ml of ethyl acetate, 2 ml of water and 4 ml of KOH (15% strength) are added dropwise with ice cooling and the mixture is stirred for 30 minutes. The salts are filtered off. After concentrating, the residue is taken up in methylene chloride, washed with water, dried and evaporated again. The residue is purified with the aid of flash chromatography on Merck silica gel 60 (CH₂Cl₂/ethyl acetate 1:1, CH₂Cl₂CH₃OH 1:1).

Yellowish-brown resin
TLC=CH₂Cl₂/CH₃OH 1:1, silica gel on aluminum foil / Merck 5562
$R_f$=0.16
Yield: 2.80 g (93% of theory)

EXAMPLE 13

3-Aminomethyl-6-fluoro-2-methyl-1,3,4,5-tetrahydrobenz-[c,d]-indole

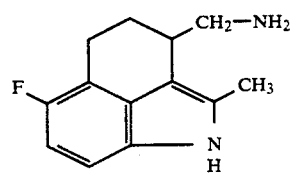

The title compound was prepared from 3.21 g (0.015 mol) of the compound from Example 11 analogously to the directions of Example 12.

M.p.: 230° C.

TLC : CH$_2$Cl$_2$ ethyl acetate 1:1, silica gel on aluminum foil / Merck 5562

R$_f$=0.20

Yield: 68.8%

EXAMPLE 14

2-Methyl-3-(4-toluenesulphonyl -aminomethyl-1,3,4,5-tetrahydro-benz-[c,d]-indole

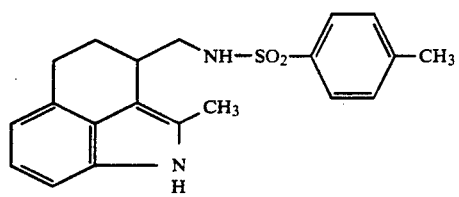

3.00 g (0.015 mol) of 3-aminomethyl-2-methyl-1,3,4,5-tetrahydro-benz-[c,d]-indole and 5 mol of triethylamine are dissolved in 100 ml of methylene chloride. 2.86 g (0.015 mol) of p-toluenesulphonyl chloride are then dissolved and added dropwise in 40 ml of methylene chloride in the course of 30 minutes. The reaction mixture is subsequently stirred at room temperature for 2 hours. It is then extracted by shaking with 1 N hydrochloric acid, then with water. The organic phase is dried over magnesium sulphate and evaporated in vacuo. The residue obtained is made to crystallize using isopropanol. The precipitate is filtered off with suction, washed with isopropanol and diethyl ether and dried in a high vacuum at 50° C.

Yield: 3.96 g (74.7% of theory)

Melting point: 211° C.

R$_f$ value: 0.48 (silica gel on aluminum foil Merck 5562, mobile phase toluene/ethyl acetate 3:1)

The Examples shown in the following tables were prepared analogously to Example 14.

TABLE 1

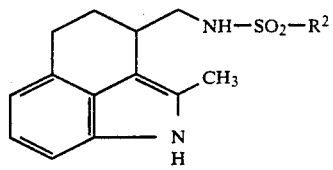

| Ex: | R$^2$ | m.p. | R$_f$(toluene/ethyl acetate = 3:1) | |
|---|---|---|---|---|
| 15 | –⌬ | 152° C. | 0.51 | silica gel on aluminum foil Merck 5562 |
| 16 | –⌬–F | 156° C. | 0.49 | |
| 17 | –⌬–Br | 214° C. | 0.57 | |
| 18 | –⌬–Cl | 201° C. | 0.52 | |
| 19 | –⌬–OCH$_3$ | 191° C. | 0.41 | |
| 20 | naphthyl | 128° C. | 0.57 | |

TABLE 2

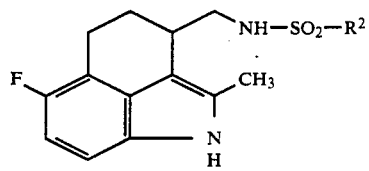

| Ex. | R$^2$ | m.p. | R$_f$(toluene/ethyl acetate = 3:1) | |
|---|---|---|---|---|
| 21 | –⌬–F | 123° C. | 0.40 | silica gel on aluminum foil Merck 5562 |
| 22 | –⌬–Cl | 156° C. | 0.50 | |
| 23 | –⌬–Br | 161° C. | 0.47 | |
| 24 | –⌬–OCH$_3$ | 148° C. | 0.35 | |
| 25 | –⌬ | 170° C. | 0.41 | |
| 26 | –⌬–CH$_3$ | 173° C. | 0.44 | |

EXAMPLE 27

1-(2-Cyanoethyl)-3-[N-(2-cyanoethyl)-N-(4-toluenesulphonyl)-aminomethyl]-2-methyl-1,3,4,5-tetrahydro-benz-[c,d]-indole

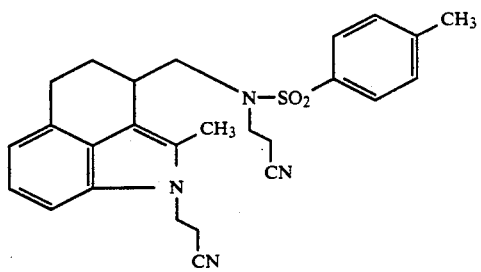

3.86 g (0.01 mol) of 2-methyl-3-(4-toluenesulphonyl)-aminomethyl-1,3,4,5-tetrahydro-benz-[c,d]-indole are dissolved in 50 ml of absolute 1,4-dioxane and 4 ml of acrylonitrile and 4 drops of benzyltrimethylammonium hydroxide solution (40% strength in methanol) are added successively. The mixture is subsequently stirred at 80° C. for 3 hours. It is then taken up in ethyl acetate after evaporating the solvent and extracted by shaking twice with water. The organic phase is dried over magnesium sulphate and evaporated. The residue is made to crystallize using methanol. The precipitate is subsequently filtered off with suction, washed with methanol and dried in a high vacuum at 50° C.

Yield: 4.47 g (89.2% of theory)
Melting point: 163° C.
$R_f$ value: 0.20 (silica gel on aluminum foil Merck 5562, mobile phase toluene/ethyl acetate 6:1)

The examples shown in the following tables are prepared analogously to Example 27:

TABLE 3

| Ex. | $R^2$ | m.p. | $R_f$(toluene/ethyl acetate = 6:1) | |
|---|---|---|---|---|
| 28 | phenyl | 178° C. | 0.18 | silica gel on aluminum foil Merck 5562 |
| 29 | 4-F-phenyl | 206° C. | 0.17 | |
| 30 | 4-Br-phenyl | 140° C. | 0.24 | |
| 31 | 4-Cl-phenyl | 124° C. | 0.21 | |
| 32 | 4-OCH$_3$-phenyl | 146° C. | 0.13 | |
| 33 | 1-naphthyl | 102° C. | 0.22 | |

TABLE 4

| Ex. | $R^2$ | m.p. | $R_f$(toluene/ethyl acetate = 6:1) | |
|---|---|---|---|---|
| 34 | 4-F-phenyl | 153° C. | 0.28 | silica gel on aluminum foil Merck 5562 |
| 35 | 4-Cl-phenyl | 130° C. | 0.32 | |
| 36 | 4-Br-phenyl | 128° C. | 0.33 | |
| 37 | 4-OCH$_3$-phenyl | 152° C. | 0.19 | |
| 38 | phenyl | 166° C. | 0.20 | |

TABLE 4-continued

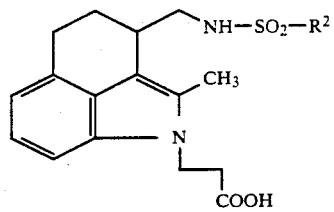

| Ex: | R² | m.p. | R_f (toluene/ethyl acetate = 6:1) |
|---|---|---|---|
| 39 | —⟨phenyl⟩—CH₃ | 118° C. | 0.29 |

EXAMPLE 40

2-Methyl-3-(4-toluenesulphonyl)-aminomethyl-1,3,4,5-tetrahydro-1-benz-[c,d]-indolepropionic acid

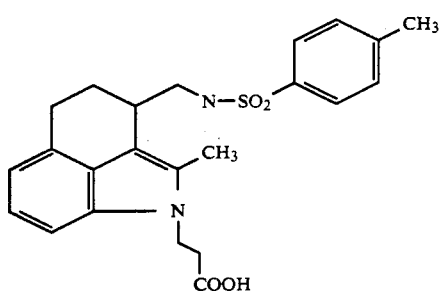

15 g of potassium hydroxide and 85 ml of water are added to 4.38 g (0.0095 mol) of 1-(2-cyanoethyl)-3-[N-(2-cyano-ethyl)-N-(4-toluenesulphonyl)-aminomethyl]-2-methyl-1,3,4,5-tetrahydro-benz-[c,d]-indole and the mixture is stirred vigorously under reflux for 6 hours. The mixture is subsequently rendered acidic using 6 N hydrochloric acid with ice cooling and then extracted 3 times with methylene chloride. The combined organic phases are washed once with water, dried over magnesium sulphate and evaporated in vacuo. The residue is made to crystallize by stirring with toluene. It is filtered off with suction, washed with toluene and n-pentane and dried at 50° C. in a high vacuum.

Yield: 4.05 g (100% of theory)

Melting point: 154° C.

R_f value: 0.54 (silica gel on aluminum foil Merck 5562, mobile phase toluene/ethanol 3:1)

The examples shown in the following tables are prepared analogously to Example 40:

TABLE 5

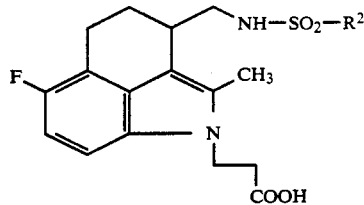

| Ex: | R² | m.p. | R_f (toluene/ethyl acetate = 3:1) |
|---|---|---|---|
| 41 | —⟨phenyl⟩ | 118° C. | 0.54 silica gel on aluminum foil Merck 5562 |
| 42 | —⟨phenyl⟩—F | 154° C. | 0.58 |
| 43 | —⟨phenyl⟩—Br | 162° C. | 0.56 |
| 44 | —⟨phenyl⟩—Cl | 172° C. | 0.50 |
| 45 | —⟨phenyl⟩—OCH₃ | 104° C. | 0.51 |
| 46 | —⟨naphthyl with CH₃⟩ Na Salt | 66° C. | 0.53 |

TABLE 6

[structure: F-substituted tetrahydrobenz[c,d]indole with NH—SO₂—R², CH₃, N—CH₂CH₂—COOH]

| Ex. | R² | m.p. | R_f (toluene/ethyl acetate = 3:1) |
|---|---|---|---|
| 47 | —⟨phenyl⟩—F | 124° C. | 0.47 silica gel on aluminum foil Merck 5562 |
| 48 | —⟨phenyl⟩—Cl | 115° C. | 0.53 |

TABLE 6-continued

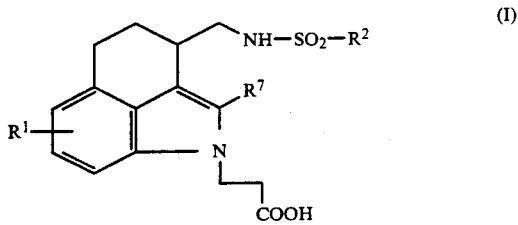

| Ex. | R² | m.p. | R_f (toluene/ethyl acetate = 3:1) |
|---|---|---|---|
| 49 | —⟨phenyl⟩—Br | 108° C. | 0.45 |
| 50 | —⟨phenyl⟩—OCH₃ | 155° C. | 0.46 |
| 51 | —⟨phenyl⟩ | 157° C. | 0.44 |
| 52 | —⟨phenyl⟩—CH₃ | 157° C. | 0.49 |

USE EXAMPLE 53

In order to determine the thrombocyte aggregation-inhibiting effect, blood from healthy subjects of both sexes was used. One part of 3.8% strength aqueous sodium citrate solution was mixed with 9 parts of blood as an anticoagulant. Platelet-rich citrate plasma (PRP) was obtained from this blood by means of centrifugation (Jurgens/Beller, Klinische Methoden der Blutgerinnungs-analyse; (Clinical Methods of Blood Coagulation Analysis); Thieme Verlag, Stuttgart, 1959).

For these investigations, 0.8 ml of PRP and 0.1 ml of the active compound solution were preincubated in a water bath at 37° C. Thrombocyte aggregation was subsequently determined by the turbidimetric method (Born, G.V.R., J. Physiol. (London), 162, 67, 1962) in an aggregometer at 37° C. (Therapeutische Berichte 47, 80–86, 1975). To this end, 0.1 ml of collagen, an aggregation-inducing agent, was added to the preincubated sample. The change of optical density in the sample of PRP was recorded during a period of 6 minutes and the result was determined after 6 minutes. To this end, the percentage inhibition compared to the control is calculated. The range of the minimum effective concentration is indicated as the threshold concentration.

The threshold concentration are in between 0.003–10mg/1.

For Example 18 by way of example:

EC=0.01–0.003 mg/1.

It will be appreciated that the instant specification and claims are set forth by way of illustration and not limitation, and that various modifications and changes may be made without departing from the spirit and scope of the present invention.

We claim:

1. A tetrahydro-1-benz-[c,d]-indolepropionic acid sulphonamide of the formula (I)

[structure with R¹, R⁷, NH—SO₂—R², COOH]

in which
R¹-represents hydrogen, fluorine, chlorine, bromine, trifluoromethyl, carboxyl or lower alkoxycarbonyl, or
—represents a group —S(O)$_n$R³, —NR⁴R⁵ or OR⁶,
in which
R³- is lower alkyl or phenyl,
R⁴ and R⁵ are identical or different and are hydrogen, lower alkyl, phenyl or benzyl,
R⁶—is hydrogen, lower alkyl, phenyl benzyl or trifluoromethyl,
and
n—is a number 0, 1 or 2,
or
R¹- represents lower alkyl, lower alkenyl, cyclopropyl, cyclopentyl or cyclohexyl, which is unsubstituted or substituted by carboxyl, lower alkoxy, fluorine, chlorine, bromine, hydroxyl, lower alkoxycarbonyl, lower alkylthio or cyano,
and
R²- represents phenyl or naphthyl, which is monosubstituted to trisubstituted by identical or different substituents selected from the group consisting of fluorine, chlorine, bromine, cyano, trifluoromethyl, trifluoromethoxy, trifluoro methylthio, lower alkyl, carboxymethyl, carboxyethyl, methoxycarbonylmethyl, methoxycarbonylmethyl, ethoxycarbonylmethyl, methoxycarbonylethyl, lower alkoxy, lower alkylthio, hydroxyl, carboxyl, lower alkoxycarbonyl, phenyl, phenoxy, benzyloxy, benzylthio and —NR⁴R⁵, and
R⁷- represents hydrogen, lower alkyl, cyclopropyl, cyclopentyl or cyclohexyl,
or a salt thereof.

2. A tetrahydro-1-benz-[c,d]-indolepropionic acid sulphonamide or salt thereof according to claim 1, in which
R¹- represents hydrogen, fluorine, chlorine, bromine, trifluoromethyl, methylthio, ethylthio, methylsulphonyl, ethylsulphonyl, phenylthio, phenylsulphonyl, amino, dimethylamino or diethylamino,
or
- represents a group —OR⁶,
in which
R⁶- is hydrogen, methyl, ethyl, propyl, phenyl or benzyl,
or
- represents methyl, ethyl, propyl or isopropyl, and
R²- represents phenyl or naphthyl, which is monosubstituted or disubstituted by identical or different substituents selected from the group consisting of fluorine, chlorine, bromine, cyano, trifluoromethyl, trifluoromethoxy, methyl, ethyl, propyl, methoxy, ethoxy, propoxy, methylthio, hydroxyl, methoxycarbonyl, ethoxycarbonyl, phenyl, dimethylamino and diethylamino, and R⁷- represents hydrogen or methyl.

3. A compound according to claim 1, wherein such compound is 2-methyl-3-benzenesulphonyl-aminomethyl-1,3,4,5-tetrahydro-benz-[c,d]-indolepropionic acid of the formula

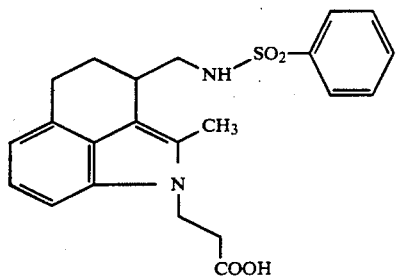

or a salt thereof.

4. A compound according to claim 1, wherein such compound is 2-methyl-3-(4-fluorophenylsulphonyl)-aminomethyl-1,3,4,5-tetrahydro-benz-[c,d]-indolepropionic acid of the formula

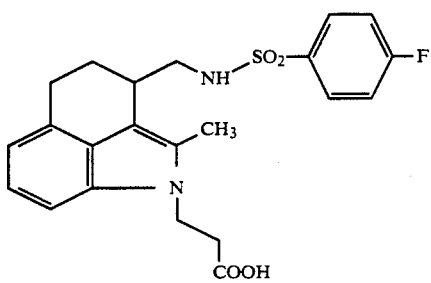

or a salt thereof.

5. A compound according to claim 1, wherein such compound is 2-methyl-3-(4-bromophenylsulphonyl)-aminomethyl-1,3,4,5-tetrahydro-benz-[c,d]-indolepropionic acid of the formula

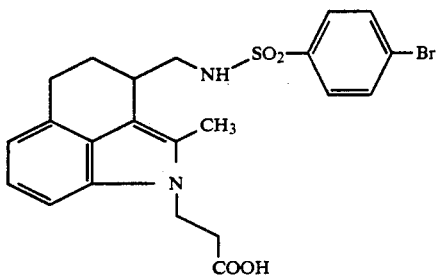

or a salt thereof.

6. A compound according to claim 1, wherein such compound is 2-methyl-3-(4-chlorophenylsulphonyl)-aminomethyl-1,3,4,5-tetrahydro-benz-[c,d]-indolepropionic acid of the formula

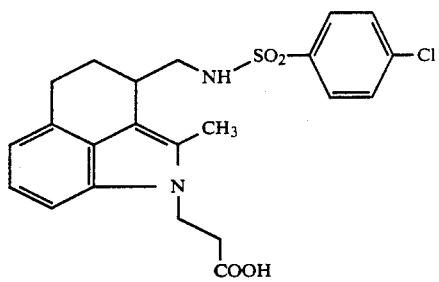

or a salt thereof.

7. A compound according to claim 1, wherein such compound is 2-methyl-3-(4-fluorophenylsulphonyl)-aminomethyl-6-fluoro-1,3,4,5-tetrahydro-benz-[c,d]-indolepropionic acid of the formula

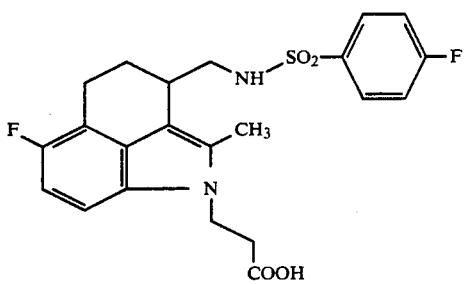

or a salt thereof.

8. A compound according to claim 1, wherein such compound is 2-methyl-3-(4-chlorophenylsulphonyl)-aminomethyl-6-fluoro-1,3,4,5-tetrahydro-benz-[c,d]-indoleproprionic acid of the formula

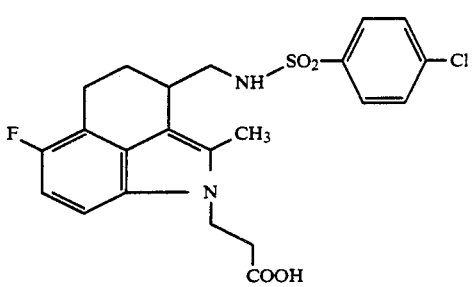

or a salt thereof.

9. A thrombocyte aggregating-inhibiting composition comprising an amount effective therefor of a compound or salt according to claim 1 and a diluent.

10. A unit dose of a composition according to claim 9 in the form of a tablet, capsule or ampoule.

11. A method of inhibiting thrombocyte aggregation in a patient in need thereof which comprises administering to such patient an amount effective therefor of a compound or salt according to claim 1.

12. The method according to claim 11, wherein such compound is 2-methyl-3-benzenesulphonyl-aminomethyl-1,3,4,5-tetrahydro-benz-[c,d]-indolepropionic acid,
2-methyl-3-(4-fluorophenylsulphonyl)-aminomethyl-1,3,4,5-tetrahydro-benz-[c,d]-indolepropionic acid,
2-methyl-3-(4-bromophenylsulphonyl)-aminomethyl-1,3,4,5-tetrahydro-benz-[c,d]-indolepropionic acid, 2-methyl-3-(4-chlorophenylsulphonyl)-aminomethyl-1,3,4,5-tetrahydro-benz-[c,d]-indolepropionic acid,
2-methyl-3-(4-fluorophenylsulphonyl)-aminomethyl-6-fluoro-1,3,4,5-tetrahydro-benz-[c,d]-indolepropionic acid, or
2-methyl-3-(4-chlorophenylsulphonyl)-aminomethyl-6-fluoro-1,3,4,5-tetrahydro-benz-[c,d]-indolepropionic acid.

13. A tetrahydro-1-benz-[c,d]-indolepropionic acid sulphonamide of the formula

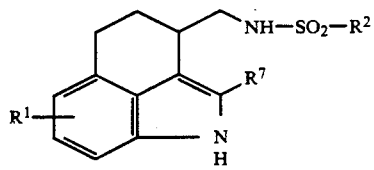

in which

R$^1$- represents hydrogen, fluorine, chlorine, bromine, trifluoromethyl, carboxyl or lower alkoxycarbonyl, or - represents a group —S(O)$_n$R$^3$, —NR$^4$R$^5$ or OR$^6$, in which R$^3$- is lower alkyl or phenyl, R$^4$ and R$^5$ are identical or different and are hydrogen, lower alkyl, phenyl or benzyl, R$^6$- is hydrogen, lower alkyl, phenyl benzyl or trifluoromethyl, and n - is a number 0 or 2, or R$^1$- represents lower alkyl, lower alkenyl, cyclopropyl, cyclopentyl or cyclohexyl, which is unsubstituted or substituted by carboxyl, lower alkoxy, fluorine, chlorine, bromine, hydroxyl, lower alkoxycarbonyl, lower alkythio or cyano, and R$^2$- represents phenyl or naphthyl, which is monosubstituted to trisubstituted by identical or different substituents selected from the group consisting of fluorine, chlorine, bromine, cyano, trifluoromethyl, trifluoromethoxy, trifluoro methylthio, lower alkyl, carboxymethyl, carboxyethyl, methoxycarbonylmethyl, methoxycarbonylmethyl, ethoxycarbonylmethyl, methoxycarbonylethyl, lower alkoxy, lower alkylthio, hydroxyl, carboxyl, lower alkoxycarbonyl, phenyl, phenoxy, benzyloxy, benzylthio and —NR$^4$R$^5$, and R$^7$- represents hydrogen, lower alkyl, cyclopropyl, cyclopentyl or cyclohexyl.

14. A thrombocyte aggregating-inhibiting composition consisting essentially of an amount effective therefor of a compound or salt according to claim 13 and a diluent.

15. A unit dose of a composition according to claim 13 in the form of a tablet, capsule or ampoule.

16. A method of inhibiting thrombocyte aggregation in a patient in need thereof which comprises administering to such patient an amount effective therefor of a compound or salt according to claim 13.

17. The method according to claim 16, wherein such compound is 2-methyl-3-benzenesulphonyl-aminomethyl-1,3,4,5-tetrahydro-benz-[c,d]-indole, 2-methyl-3-(4-fluorophenylsulphonyl)-aminomethyl-1,3,4,5-tetrahydro-benz-[c,d]-indole,
2-methyl-3-(4-bromophenylsulphonyl)-aminomethyl-1,3,4,5-tetrahydro-benz-[c,d]-indole,
2-methyl-3-(4-chlorophenylsulphonyl)-aminomethyl-1,3,4,5-tetrahydro-benz-[c,d]-indole,
2-methyl-3-(4-fluorophenylsulphonyl)-aminomethyl-6-fluoro-1,3,4,5-tetrahydro-benz-[c,d]-indole, and
2-methyl-3-(4-chlorophenylsulphonyl)-aminomethyl-6-fluoro-1,3,4,5-tetrahydro-benz-[c,d]-indole.

18. A tetrahydro-1-benz-[c,d]-indolepropionic acid sulphonamide or salt thereof according to claim 17, in which R$^1$- represents hydrogen, fluorine, chlorine, bromine, trifluoromethyl, methylthio, ethylthio, methylsulphonyl, ethylsulphonyl, phenylthio, phenylsulphonyl, amino, dimethylamino or diethylamino, or

- represents a group —OR$^6$, in which

R$^6$- is hydrogen, methyl, ethyl, propyl, phenyl or benzyl, or

- represents methyl, ethyl, propyl or isopropyl, and

R$^2$- represents phenyl or naphthyl, which is monosubstituted or disubstituted by identical or different substituents selected from the group consisting of fluorine, chlorine, bromine, cyano, trifluromethyl, trifluoromethoxy, methyl, ethyl, propyl, methoxy, ethoxy, propoxy, methylthio, hydroxyl, methoxycarbonyl, ethoxycarbonyl, phenyl, dimethylamino and diethylamino, and R$^7$- represents hydrogen or methyl.

19. A compound according to claim 7, wherein such compound is 2-methyl-3-benzenesulphonyl-aminomethyl-1,3,4,5-tetrahydro-benz-[c,d]-indole of the formula

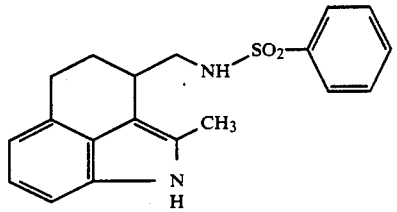

or a salt thereof.

20. A compound according to claim 17 wherein such compound is 2-methyl-3-(4-fluorophenylsulphonyl)-aminomethyl-1,3,4,5-tetrahydro-benz-[c,d]-indole of the formula

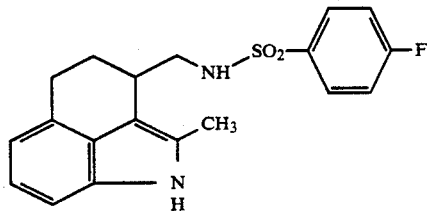

or a salt thereof.

21. A compound according to claim 17, wherein such compound is 2-methyl-3-(4-bromophenylsulphonyl)-aminomethyl-1,3,4,5-tetrahydro-benz-[c,d]-indole of the formula

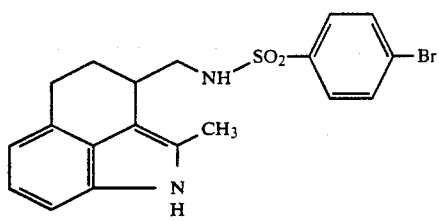

or a salt thereof.

22. A compound according to claim 17, wherein such compound is 2-methyl-3-(4-chlorophenylsulphonyl)-aminomethyl-1,3,4,5-tetrahydro-benz-[c,d]-indole of the formula

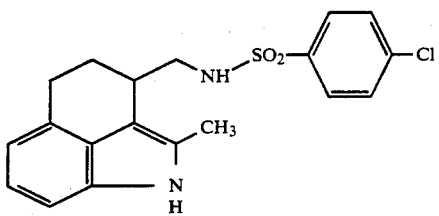

or a salt thereof.

23. A compound according to claim 17, wherein such compound is 2-methyl-3-(4-fluorophenylsulphonyl)-aminomethyl-6-fluoro-1,3,4,5-tetrahydro-benz-[c,d]-indole of the formula

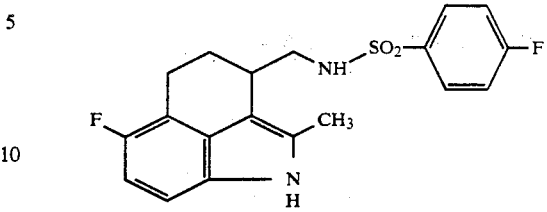

or a salt thereof.

24. A compound according to claim 17, wherein such compound is 2-methyl-3-(4-chlorophenylsulphonyl)-aminomethyl-6-fluoro-1,3,4,5-tetrahydro-benz-[c,d]-indole of the formula

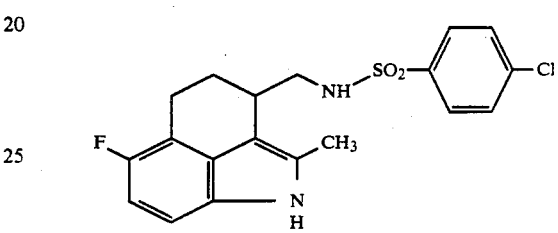

or a salt thereof.

* * * * *

UNITED STATES PATENT AND TRADEMARK OFFICE
CERTIFICATE OF CORRECTION

PATENT NO. : 5,079,258

DATED : January 7, 1992

INVENTOR(S) : Boshagen et al.

It is certified that error appears in the above-identified patent and that said Letters Patent is hereby corrected as shown below:

Col. 25, line 39  Delete " alkythio " and substitute -- alkylthio --

Col. 26, line 12  Delete " 17 " and substitute -- 13 --

Col. 26, line 35  Delete " 7 " and substitute -- 13 --

Col. 26, line 49  Delete " 17 " and substitute -- 13 --

Col. 26, line 65  Delete " 17 " and substitute -- 13 --

Col. 27, line 13  Delete " 17 " and substitute -- 13 --

Col. 27, line 29  Delete " 17 " and substitute -- 13 --

Col. 28, line 15  Delete " 17 " and substitute -- 13 --

Signed and Sealed this

Thirty-first Day of August, 1993

*Attest:*

BRUCE LEHMAN

*Attesting Officer*        *Commissioner of Patents and Trademarks*